United States Patent
Aoki et al.

(10) Patent No.: US 11,980,559 B2
(45) Date of Patent: May 14, 2024

(54) LEG BRACE

(71) Applicant: Toyota Jidosha Kabushiki Kaisha, Toyota Aichi-ken (JP)

(72) Inventors: Eisuke Aoki, Toyota (JP); Takahiro Takeda, Toyota (JP); Seiichi Tanabe, Toyota (JP); Tomio Ikeda, Toyota (JP); Tadashi Odashima, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 450 days.

(21) Appl. No.: 17/177,743

(22) Filed: Feb. 17, 2021

(65) Prior Publication Data
US 2021/0259868 A1    Aug. 26, 2021

(30) Foreign Application Priority Data

Feb. 21, 2020    (JP) ................ 2020-028584

(51) Int. Cl.
| | |
|---|---|
| A61F 5/01 | (2006.01) |
| A43B 7/14 | (2022.01) |
| A43B 7/1405 | (2022.01) |
| A61F 5/058 | (2006.01) |

(52) U.S. Cl.
CPC .......... *A61F 5/0111* (2013.01); *A43B 7/1405* (2013.01); *A61F 5/0585* (2013.01)

(58) Field of Classification Search
CPC ......... A43B 7/1405; A43B 7/20; A43B 7/223; A43B 7/22; A43B 5/1691; A61F 5/0111; A61F 5/0585; A61F 5/0127; A61F 2005/0165; A61F 2005/0181

See application file for complete search history.

(56) References Cited

U.S. PATENT DOCUMENTS

| | | | | |
|---|---|---|---|---|
| 3,333,353 | A * | 8/1967 | Garcia | A43B 23/22 36/76 R |
| 5,700,237 | A * | 12/1997 | Hess | A61F 5/0585 602/27 |
| 5,704,137 | A | 1/1998 | Dean et al. | |
| 8,591,446 | B2 * | 11/2013 | Helm | A61F 5/0127 602/23 |
| 9,421,117 | B1 * | 8/2016 | Hames | A61F 5/0111 |

(Continued)

FOREIGN PATENT DOCUMENTS

| | | |
|---|---|---|
| JP | H10-005006 A | 1/1998 |
| JP | 2008-515490 A | 5/2008 |

(Continued)

*Primary Examiner* — Camtu T Nguyen
(74) *Attorney, Agent, or Firm* — Dinsmore & Shohl LLP

(57) ABSTRACT

The present disclosure can provide a leg brace capable of reducing a pain in a knee while both enhancing its convenience and reducing the burden on an ankle. the leg brace including: a first pushing part that pushes a leg of the wearer outward so that an ankle bone is positioned above a heel bone; a second pushing part that pushes the leg of the wearer inward so that the ankle bone is positioned above the heel bone; a restraint part that restrains a positional relation between the first and the second pushing parts in which they face each other across the leg of the wearer; and a placement part on which a foot of the wearer is placed, the placement part being connected to the first pushing part or the second pushing part.

1 Claim, 12 Drawing Sheets

(56) References Cited

U.S. PATENT DOCUMENTS

| | | |
|---|---|---|
| 2006/0084899 A1 | 4/2006 | Verkade et al. |
| 2011/0119808 A1 | 5/2011 | Sherman |
| 2019/0116928 A1 | 4/2019 | Yahata et al. |

FOREIGN PATENT DOCUMENTS

| | | |
|---|---|---|
| JP | 4990036 B2 | 8/2012 |
| JP | 6353479 B2 | 7/2018 |
| WO | 94/16589 A1 | 8/1994 |

\* cited by examiner

LEG BRACE

CROSS REFERENCE TO RELATED APPLICATIONS

This application is based upon and claims the benefit of priority from Japanese patent application No. 2020-28584, filed on Feb. 21, 2020, the disclosure of which is incorporated herein in its entirety by reference.

BACKGROUND

The present disclosure relates to a leg brace. For example, the present disclosure relates to a leg brace that is inserted into a shoe worn by a wearer and is attached to the leg of the wearer to correct the alignment of his/her ankle bone (i.e., talus) and heel bone (i.e., calcaneus).

In recent years, a sole plate has sometimes been used to reduce a pain in the knee of a person (e.g., a patient with medial knee osteoarthritis) who suffers from knee pain. For example, Japanese Patent No. 4990036 discloses a sole brace for treatment of leg diseases configured so that it can fix a sole plate to a foot via a belt by winding the belt around the sole plate and the ankle in a state where the sole plate is set on the sole of the foot.

SUMMARY

The applicant has however found the following problem. The sole brace for treatment of leg diseases disclosed in Japanese Patent No. 4990036 has a problem that as it is necessary to fix the sole plate to the foot via the belt in order to reduce the pain in the knee of a person who suffers from knee pain, the convenience of it for users is reduced, and a large burden is imposed on the ankle.

The present disclosure has been made in view of the above-described problem and provides a leg brace capable of reducing a pain in a knee while both enhancing its convenience and reducing the burden on an ankle.

A first exemplary aspect is a leg brace that is inserted into a shoe worn by a wearer and is attached to a leg of the wearer to correct alignment of an ankle bone and a heel bone of the wearer, the leg brace including:
  a first pushing part that pushes the leg of the wearer outward so that the ankle bone is positioned above the heel bone;
  a second pushing part that pushes the leg of the wearer inward so that the ankle bone is positioned above the heel bone;
  a restraint part that restrains a positional relation between the first and the second pushing parts in which they face each other across the leg of the wearer; and
  a placement part on which a foot of the wearer is placed, the placement part being connected to the first pushing part or the second pushing part.

By such a structure, it is possible to easily attach the leg brace to the leg so that the leg is held between the first and the second pushing parts, and thus it is a highly convenient. Further, as a belt is not wound around the ankle like in the case of the sole brace for treatment of leg diseases disclosed in Japanese Patent No. 4990036, it is possible to reduce the burden on the ankle of the wearer.

Further, by arranging the ankle bone of the wearer above the heel bone thereof, a talonavicular joint axis and a calcaneocuboid joint axis are disposed substantially parallel to each other when viewed from the rear side of the wearer, whereby it is possible to enhance the rigidity of a midfoot part. As a result, a kinematic chain of the leg of the wearer is likely to occur, and when the wearer tries to pronate his/her foot or when an outer wedge insole (i.e., a sole plate) is disposed for his/her foot, the knee is internally rotated through the lower leg by the kinematic chain, so that the moment arm can be reduced. Thus, a knee *varus* moment becomes smaller than that when the wearer does not wear the leg brace, whereby it is possible to reduce a pain in the knee of the wearer.

As described above, the leg brace can reduce a pain in the knee of the wearer while enhancing its convenience and reducing the burden on the ankle.

The above-described leg brace may further include:
  a contact part that comes into contact with at least a side part of the leg of the wearer above the first and the second pushing parts; and
  a connection part that connects the contact part to the restraint part disposed on a rear side of a heel of the wearer,
  in which the connection part may be able to be deformed in a front/rear direction of the wearer and may not be able to be deformed in a left/right direction of the wearer.

In the above-described leg brace, each of the first and the second pushing parts may be formed of a pad that comes into contact with the leg of the wearer, and the restraint part may be formed of a belt wound around the leg so that the first and the second pushing parts are pushed against the leg.

The above-described leg brace may further include a first adjustment part capable of adjusting a position of the first pushing part or the second pushing part in the left/right direction of the wearer.

The above-described leg brace may further include a second adjustment part capable of adjusting a tilt angle of the first pushing part or the second pushing part with respect to the placement part.

The above-described leg brace may further include a filling part that fills an inside of the first pushing part or the second pushing part with a filler when the foot of the wearer is placed on the placement part.

In the above-described leg brace, the first pushing part may push a lower side of the ankle bone outward.

In the above-described leg brace, the second pushing part may push an upper side of the ankle bone inward.

The above-described leg brace may further include a pressing part that presses the ankle bone toward a heel side of the wearer.

The above-described leg brace may further include a third adjustment part capable of adjusting an amount of pressing of the ankle bone pressed by the pressing part.

According to the present disclosure, it is possible to provide a leg brace capable of reducing a pain in a knee while both enhancing its convenience and reducing the burden on an ankle.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Figure 1:
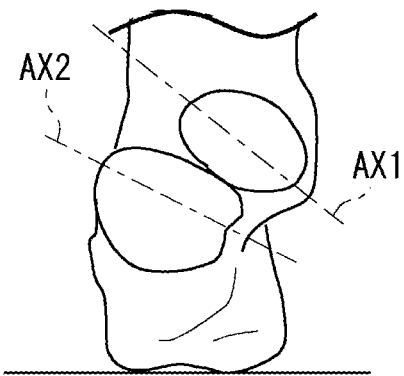
FIG. 1 is a diagram for explaining an arrangement of a talonavicular joint axis and a calcaneocuboid joint axis of a healthy person.

First, how a leg brace according to the present disclosure works for knee pain is described. An arch part is formed on the sole of a healthy person in a stance state. At this time, by the subtalar joint of the healthy person being supinated as shown in FIG. 1, a motion axis (i.e., a talonavicular joint axis) AX1 of the talonavicular joint and a motion axis (i.e., a calcaneocuboid joint axis) AX2 of the calcaneocuboid joint cross each other when viewed from the rear side of the healthy person, and consequently the movement of the subtalar joint of the healthy person is restricted.

Figure 2:
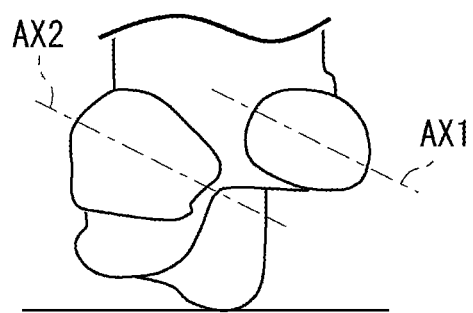
FIG. 2 is a diagram for explaining an arrangement of the talonavicular joint axis and the calcaneocuboid joint axis of a patient with medial knee osteoarthritis.

Meanwhile, for example, a patient with advanced medial knee osteoarthritis puts his/her weight on the inside of the foot in order to reduce a pain in the knee by himself/herself, and then the sole of the patient with advanced medial osteoarthritis becomes flattened in a stance state. At this time, by the subtalar joint of the patient with medial knee osteoarthritis being pronated as shown in FIG. 2, the talonavicular joint axis AX1 and the calcaneocuboid joint axis AX2 are arranged parallel to each other when viewed from the rear side of the patient with medial knee osteoarthritis, and consequently the movement of the subtalar joint of the patient with medial knee osteoarthritis is not restricted as compared to that in the case in which the talonavicular joint axis AX1 and the calcaneocuboid joint axis AX2 cross each other.

The human leg is formed so that pronation and supination of the subtalar joint are transmitted as rotation of the knee joint through the lower leg by a kinematic chain. However, when the talonavicular joint axis AX1 and the calcaneocuboid joint axis AX2 are arranged parallel to each other like in the case of a patient with medial knee osteoarthritis, pronation and supination of the subtalar joint are not transmitted as rotation of the knee joint through the lower leg.

Thus, for example, in order to reduce a pain in the knee of a patient with severe medial knee osteoarthritis who has excessive pronation of the foot, it is difficult to reduce the pain in the knee because the kinematic chain does not occur even when an attempt is made to reduce the knee *varus* moment using a sole plate or the like. Therefore, the leg brace according to the present disclosure is a leg brace that creates a state in which a kinematic chain of a leg occurs, and reduces a pain in a knee by this kinematic chain of the leg.

Specific embodiments to which the present disclosure is applied will be described hereinafter in detail with reference to the drawings. However, the present disclosure is not limited to the embodiments shown below. Further, for the clarification of the explanation, the following descriptions and the drawings are simplified as appropriate.

First Embodiment

Figure 3:
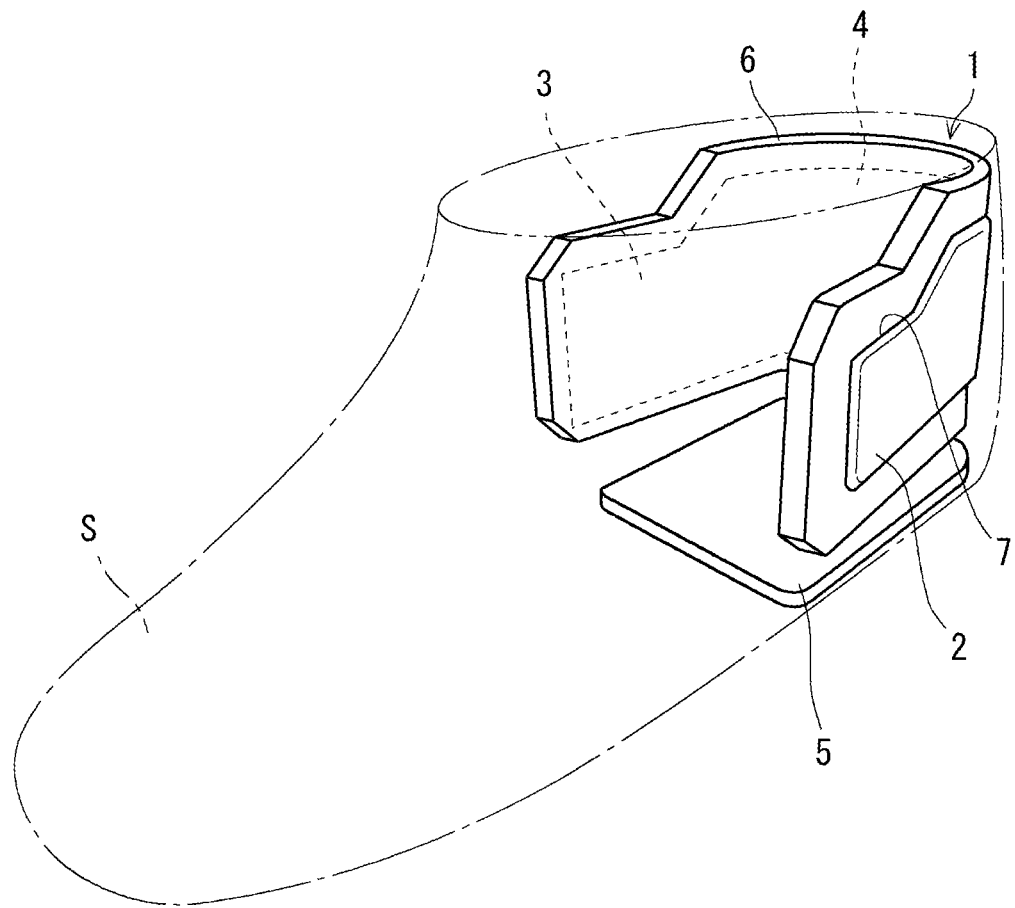
FIG. 3 is a perspective view showing a mode of use of a leg brace according to a first embodiment.
Figure 4:
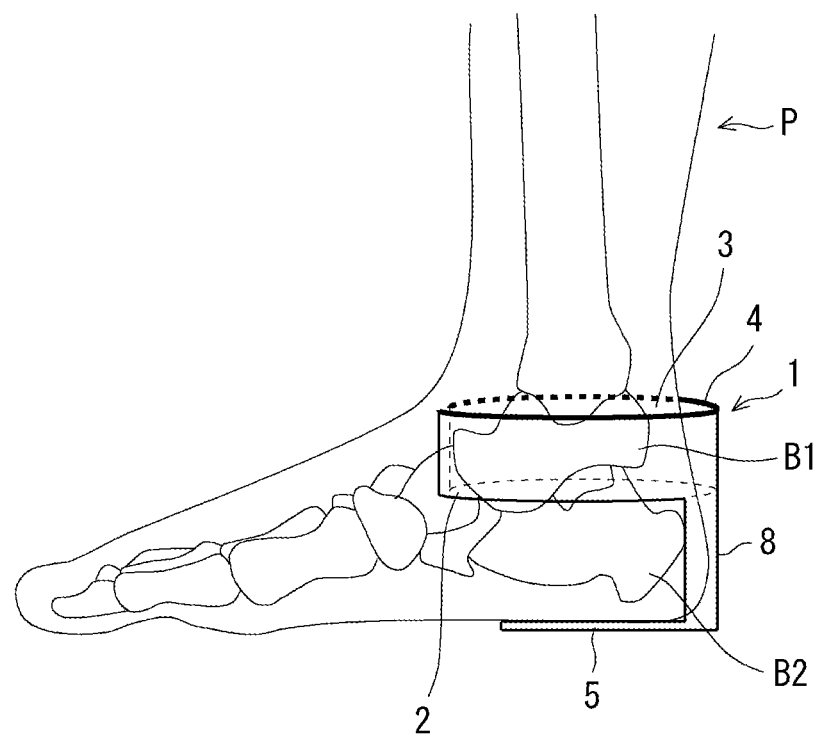
FIG. 4 is a perspective view showing a state in which the leg brace according to the first embodiment is attached to a leg of a wearer.
Figure 5:
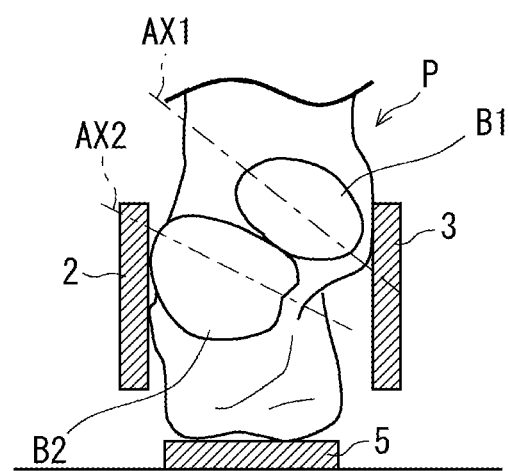
FIG. 5 is a diagram showing a state in which an ankle bone and a heel bone are held between a first pushing part and a second pushing part of the leg brace according to the first embodiment.

First, a structure of a leg brace according to this embodiment is described. FIG. 3 is a perspective view showing a mode of use of the leg brace according to this embodiment. FIG. 4 is a perspective view showing a state in which the leg brace according to this embodiment is attached to a leg of a wearer. FIG. 5 is a diagram showing a state in which an ankle bone and a heel bone are held between a first pushing part and a second pushing part of the leg brace according to this embodiment.

Note that in FIG. 3, in order to clearly show the structure of the leg brace, a shoe worn by a wearer (e.g., a patient with medial knee osteoarthritis) who wears the leg brace is shown by an alternate long and short dashed line. Further, in FIGS. 4 and 5, the shoe is omitted in order to clearly show a state in which the wearer wears the leg brace. Further, in FIGS. 4 and 5, the leg brace is simplified.

In the following description, a front/rear direction, a left/right direction, and an up/down direction are directions defined based on the wearer who wears the leg brace and is in a standing posture, and can also be referred to as directions defined based on the leg brace. However, the front/rear direction, the left/right direction, and the up/down direction are defined for the sake of convenience in order to clarify the explanation, and thus vary depending on a walking posture of the wearer. Note that in the following description, in regard to one leg to which the leg brace is attached, the other leg side of the one leg is referred to as an "inside" and the opposite side thereof is referred to as an "outside" as appropriate.

As shown in FIG. 3, a leg brace 1 is used by inserting it into a shoe S worn by the wearer in order to correct the alignment of the ankle bone and the heel bone of the wearer. As shown in FIGS. 4 and 5, the leg brace 1 includes a first pushing part 2, a second pushing part 3, a restraint part 4, and a placement part 5, and can maintain a state in which an ankle bone B1 and a heel bone B2 of a wearer P are held between the first and the second pushing parts 2 and 3. Note that the leg brace 1 according to this embodiment is attached to the right leg of the wearer P.

The first pushing part 2 pushes the ankle bone B1 and the heel bone B2 outward (i.e., to the right side) in the left/right direction of the wearer P. As shown in FIGS. 4 and 5, the first pushing part 2 is formed so that it can come into substantial surface contact with an area of the foot of the wearer P below the inner ankle, and basically has, for example, a plate body substantially perpendicular to the left/right direction of the wearer P.

The second pushing part 3 pushes the ankle bone B1 and the heel bone B2 inward (i.e., to the left side) in the left/right direction of the wearer P. As shown in FIGS. 4 and 5, the second pushing part 3 is formed so that it can come into substantial surface contact with an area of the foot of the wearer P below the outside ankle, and basically has, for example, a plate body substantially perpendicular to the left/right direction of the wearer P.

The restraint part 4 restrains a positional relation between the first pushing part 2 and the second pushing part 3 in which they face each other across the leg of the wearer P. The restraint part 4 is disposed on the rear side of the heel of the wearer P, and basically has, for example, a plate body curved along the rear side of the heel of the wearer P.

One end of the restraint part 4 is fixed to a rear end part of the first pushing part 2. Further, the other end of the restraint part 4 is fixed to a rear end part of the second pushing part 3. Thus, the first pushing part 2, the second pushing part 3, and the restraint part 4 form a substantially U-shape when viewed from the up/down direction of the wearer P.

It should be noted that as shown in FIG. 3, an elastic foam 6 such as a sponge may be provided on an inner peripheral surface of each of the first and the second pushing parts 2 and 3 and the restraint part 4. By this structure, the wearability of the leg brace 1 when the wearer P wears the leg brace 1 can be improved. Further, a notched part 7 may be formed at a corner part of the first and the second pushing parts 2 and 3 on the upper front side thereof in order to avoid interference of these parts with the ankle.

As shown in FIG. 4, the foot of the wearer P is placed on the placement part 5. The placement part 5 basically has, for example, a plate body substantially perpendicular to the up/down direction of the wearer P, and is connected to the restraint part 4 at the rear side of the heel of the wearer P via a connection part 8. The connection part 8 basically has a plate body substantially perpendicular to the front/rear direction of the wearer P, and connects a rear end part of the placement part 5 to a lower end part of the restraint part 4 at the rear side of the heel of the wearer P.

Thus, the first and the second pushing parts 2 and 3, the restraint part 4, the placement part 5, and the connection part 8 are integrally formed. Note that when the leg brace 1 is formed of a fiber material such as carbon fiber, it can be lighter than that made of metal or resin. However, the leg brace 1 may be made of metal or resin, and as will be described later, it is sufficient that the leg brace 1 has rigidity such that the first and the second pushing parts 2 and 3 can restrain the ankle bone B1 and the heel bone B2 of the wearer P.

Next, the movement of the leg of the wearer P when the leg brace 1 according to this embodiment is attached to the leg of the wearer P is described. When the wearer P wears the shoe S while putting the foot between the first and the second pushing parts 2 and 3 of the leg brace 1 in a state where the leg brace 1 is inserted into the shoe S, the foot of the wearer P is placed on the placement part 5, and as shown in FIG. 5, the ankle bone B1 and the heel bone B2 of the wearer P are held between the first and the second pushing parts 2 and 3 from the left and right directions of the wearer P.

By this structure, for example, when the wearer P is a patient with medial knee osteoarthritis, the ankle bone B1 of the wearer P is positioned above the heel bone B2, and the talonavicular joint axis AX1 and the calcaneocuboid joint axis AX2 are corrected so as to be disposed substantially in parallel when viewed from the rear side of the wearer P. Thus, it is possible to enhance the rigidity of the midfoot part.

It should be noted that the description "the ankle bone B1 is positioned above the heel bone B2" in the present disclosure means that the ankle bone B1 is positioned above the heel bone B2 so that the talonavicular joint axis AX1 and the calcaneocuboid joint axis AX2 are disposed substantially in parallel when viewed from the rear side of the wearer P, and does not mean that the ankle bone B1 is necessarily positioned just above the heel bone B2.

Therefore, a kinematic chain of the leg of the wearer P is likely to occur, and when an outer wedge insole having an inclined surface which becomes gradually lower in a direction from the outside toward the inside thereof is disposed in the shoe S worn by the wearer P, the knee is internally rotated through the lower leg by the kinematic chain, so that the moment arm can be reduced. Thus, a knee *varus* moment becomes smaller than that when the wearer P does not wear the leg brace 1, whereby it is possible to reduce a pain in the knee of the wearer P.

As described above, the leg brace 1 according to this embodiment can be easily attached to the leg so that the leg is held between the first and the second pushing parts 2 and 3, and thus it is highly convenient. Further, as a belt is not wound around the ankle like in the case of the sole brace for treatment of leg diseases disclosed in Japanese Patent No. 4990036, it is possible to reduce the burden on the ankle of the wearer P. Accordingly, the leg brace 1 according to this embodiment can reduce a pain in the knee of the wearer P while enhancing its convenience and reducing the burden on the ankle.

Further, as the leg brace 1 has a simple structure and is compact and lightweight, the load on walking of the wearer P is light.

Second Embodiment

Figure 6:
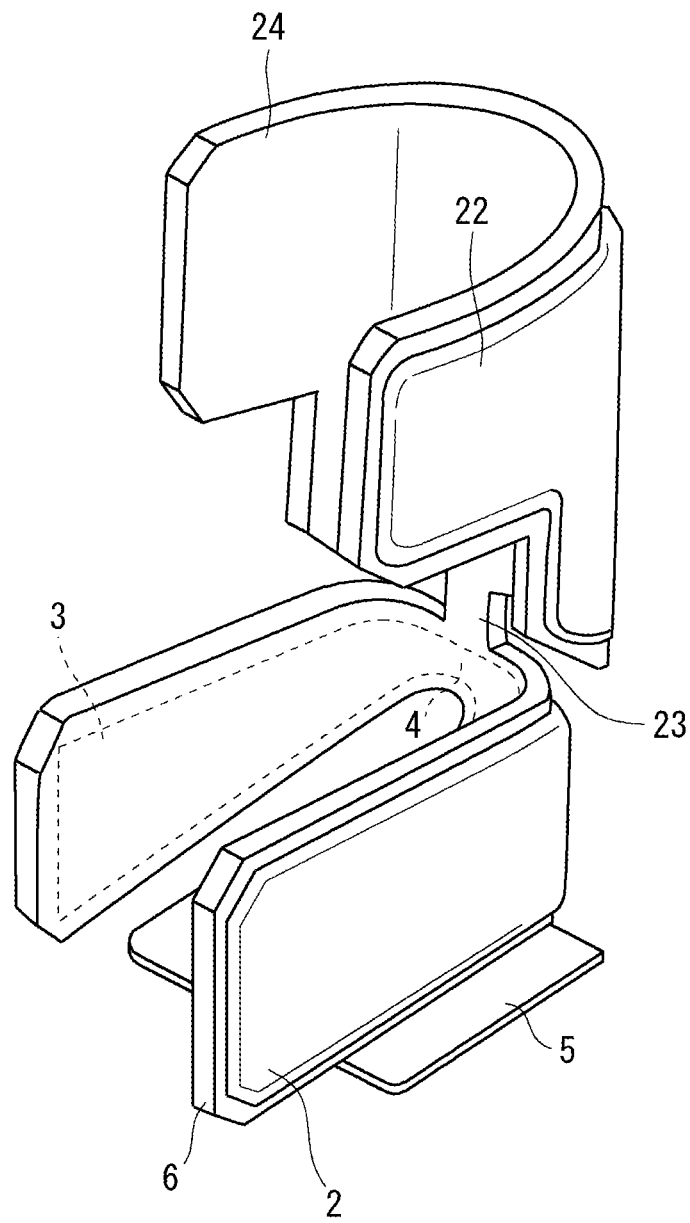
FIG. 6 is a perspective view showing a leg brace according to a second embodiment.

FIG. 6 is a perspective view showing a leg brace according to this embodiment. It should be noted that a leg brace 21 according to this embodiment has a structure substantially the same as that of the leg brace 1 according to the first embodiment, and thus redundant descriptions are omitted and the same members are described using the same reference symbols.

As shown in FIG. 6, the leg brace 21 according to this embodiment includes a contact part 22 and a second connection part 23 in addition to the first and the second pushing parts 2 and 3, the restraint part 4, the placement part 5, and the connection part (a first connection part) 8.

The contact part 22 comes into contact with at least a side part of the leg of the wearer P above the first and the second pushing parts 2 and 3. The contact part 22 basically has, for example, a U-shaped plate body having an opening in the front side thereof when viewed from the up/down direction, and comes into contact with the lower leg of the wearer P on the right and left sides thereof above the first and the second pushing parts 2 and 3. At this time, an elastic foam 24 such as a sponge may be provided on the inner peripheral surface of the contact part 22 in order to improve the wearability of the leg brace 21.

The second connection part 23 is disposed on the rear side of the leg of the wearer P, and connects the restraint part 4 to the contact part 22. The second connection part 23 basically has a plate body substantially perpendicular to the front/rear direction of the wearer P, and has a low rigidity in the front/rear direction of the wearer P and a high rigidity in the left/right direction of the wearer P. Therefore, the second connection part 23 can be deformed in the front/rear direction of the wearer P, and cannot be substantially deformed in the left/right direction of the wearer P.

In the leg brace 21 described above, as the distance between the placement part 5 and the contact part 22 is longer than the distance between the placement part 5 and the first and the second pushing parts 2 and 3, the swinging of the leg brace 21 in the left/right direction can be prevented as compared to that in the case of the leg brace 1.

Therefore, the ankle bone B1 and the heel bone B2 of the wearer P can be satisfactorily held between the first and the second pushing parts 2 and 3 from the left and right directions of the wearer P, and thus the alignment of the ankle bone B1 and the heel bone B2 of the wearer P can be satisfactorily corrected.

Further, the rigidity of the second connection part 23 in the front/rear direction of the wearer P is low, and thus walking of the wearer P is not interrupted.

Note that the structures of the contact part 22 and the second connection part 23 are not limited to the above-described structures, and may instead be any structure in which a reaction force can be obtained from a side part of the leg of the wearer P above the first and the second pushing parts 2 and 3 so that the swinging of the leg brace 21 in the left/right direction can be prevented.

Third Embodiment

Figure 7:
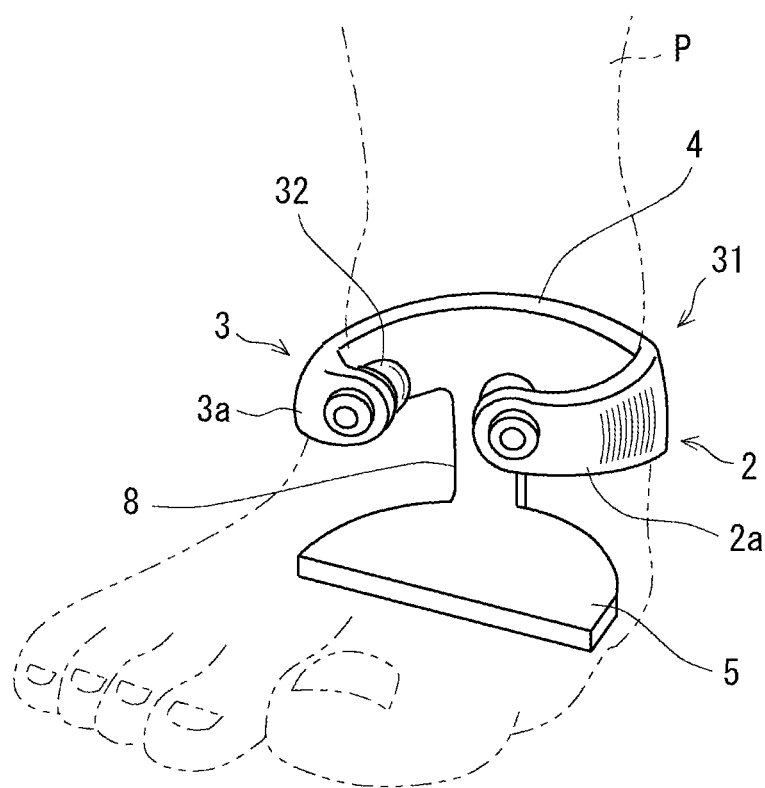
FIG. 7 is a perspective view showing a state in which a leg brace according to a third embodiment is attached to the leg of the wearer.

FIG. 7 is a perspective view showing a state in which a leg brace according to this embodiment is attached to the leg of the wearer. Note that in FIG. 7, a shoe is omitted in order to clearly show a state in which the wearer wears the leg brace. Further, in FIG. 7, in order to clearly show the structure of the leg brace, the wearer is shown by an alternate long and two short dashes line. It should be noted that a leg brace 31 according to this embodiment has a structure substantially the same as that of the leg brace 1 according to the first embodiment, and thus redundant descriptions are omitted and the same members are described using the same reference symbols.

As shown in FIG. 7, the leg brace 31 according to this embodiment has a structure in which the ankle bone B1 of the wearer P can be pressed toward the heel side (the side obliquely below and behind the wearer P), and includes a pressing part 32 in addition to the first and the second pushing parts 2 and 3, the restraint part 4, the placement part 5, and the connection part 8.

In this case, a protruding part 2a protruding to the front side of the wearer P may be provided on the front end part of the first pushing part 2. The protruding part 2a basically has a curved plate body that can cover the front inside part of the ankle of the wearer P from the front side thereof.

Further, a protruding part 3a protruding to the front side of the wearer P may be provided on the front end part of the second pushing part 3. The protruding part 3a basically has a curved plate body that can cover the front outside part of the ankle of the wearer P from the front side thereof. There is a gap between the front end edge of the protruding part 2a and the front end edge of the protruding part 3a.

It should be noted that the protruding part 2a of the first pushing part 2 and the protruding part 3a of the second pushing part 3 may be elastically deformable so that the wearer P can put the ankle through the gap between the protruding parts 2a and 3a when he/she wears the leg brace 31.

The pressing part 32 presses the ankle bone B1 of the wearer P toward the heel side. The pressing part 32 is, for example, a substantially hemispherical resin member, and is provided at the tip of each of the protruding part 2a of the first pushing part 2 and the protruding part 3a of the second pushing part 3 so that it protrudes from each of the protruding part 2a of the first pushing part 2 and the protruding part 3a of the second pushing part 3 toward the heel side.

By the structure described above, when a person whose ankle bone B1 protrudes forward wears the leg brace 31, the ankle bone B1 of the wearer P is pressed toward the heel side by the pressing part 32 and thus the movable range of an ankle dorsiflexion motion can be widened.

Further, the position of the ankle bone B1 of the wearer P is restrained by the first and the second pushing parts 2 and 3, and thus the ankle bone B1 can be satisfactorily pressed toward the heel side by the pressing part 32.

Note that the structure of the pressing part 32 is not limited to the above-described structure, and may instead be any structure in which the ankle bone B1 of the wearer P can be pressed toward the heel side, and for example, the pressing part 32 may be a belt by which the ankle of the wearer P is wound around from the front side thereof to push the ankle bone B1.

Figure 8:
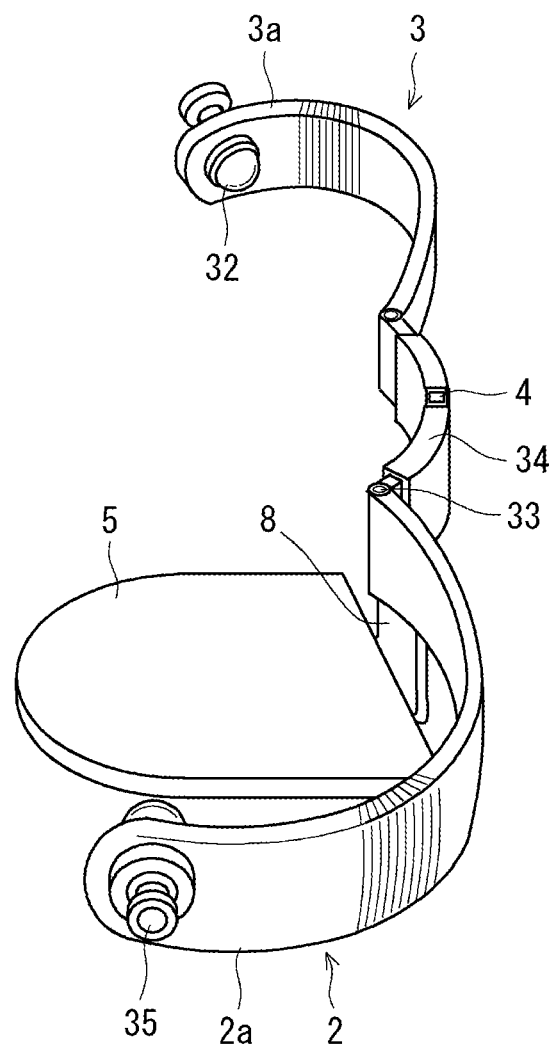
FIG. 8 is a perspective view showing another leg brace according to the third embodiment.

Further, as shown in FIG. 8, the first and the second pushing parts 2 and 3 may be connected to the restraint part 4 via a hinge 33, so that the first and the second pushing parts 2 and 3 can be opened and closed.

Figure 9:
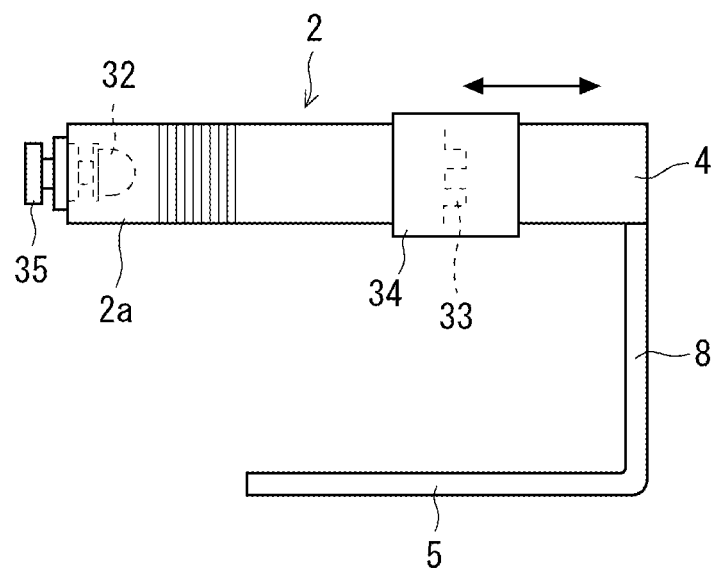
FIG. 9 is a diagram for explaining a configuration for restraining and allowing rotation of the first and the second pushing parts in the other leg brace according to the third embodiment.

At this time, as shown in FIG. 9, for example, when the hinge 33 is covered with a cylindrical restraint member 34 which has been previously passed through the first pushing part 2 and the restraint part 4 and through the second pushing part 3 and the restraint part 4, it is possible to restrain the rotation of each of the first and the second pushing parts 2 and 3 in a closed state. Meanwhile, when the restraint member 34 is slid, the rotation of each of the first and the second pushing parts 2 and 3 can be allowed so that they are opened.

By the above structure, it is possible to easily wear the leg brace 31. Further, as compared to the case where the first and the second pushing parts 2 and 3 are elastically deformable, the rigidity of each of the first and the second pushing parts 2 and 3 can be increased, and thus the ankle bone B1 can be firmly pressed toward the heel side by the pressing part 32.

Further, as shown in FIGS. 8 and 9, the leg brace 31 may include an adjustment part 35 capable of adjusting the amount of pressing of the ankle bone B1 pressed by the pressing part 32. The adjustment part 35 is, for example, a bolt with a knob screwed into a screw hole formed in each of the protruding part 2a of the first pushing part 2 and the protruding part 3a of the second pushing part 3, and the pressing part 32 is fixed to the tip of the adjustment part 35. By this structure, it is possible to adjust the position of the pressing part 32 in accordance with the degree of protrusion of the ankle bone B1 of each individual wearer P.

Fourth Embodiment

Figure 10:
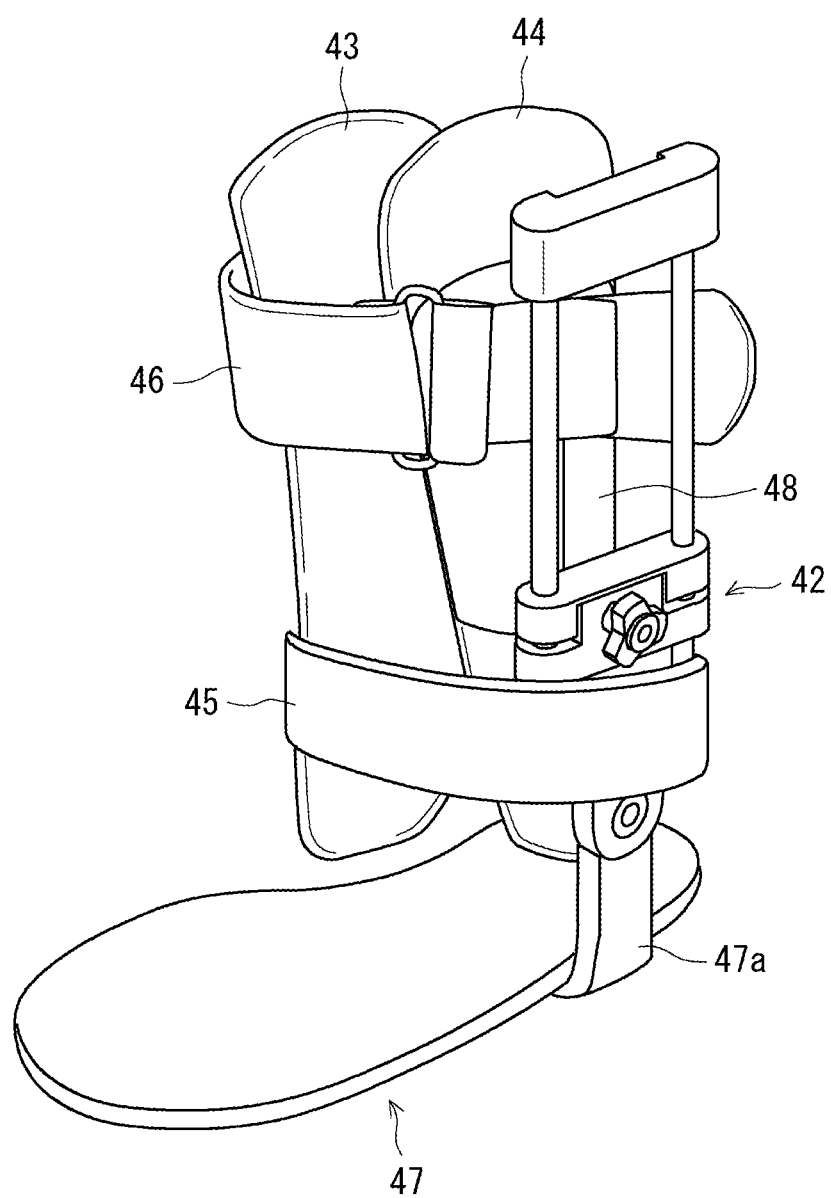
FIG. 10 is a perspective view showing a leg brace according to a fourth embodiment.

FIG. 10 is a perspective view showing a leg brace according to this embodiment. As shown in FIG. 10, a leg brace 41 according to this embodiment includes a lower leg assisting part 42, a first pushing part 43, a second pushing part 44, a first restraint part 45, and a second restraint part 46. Note that the leg brace 41 according to this embodiment is attached to the left leg of the wearer P.

The lower leg assisting part 42 is, for example, a lower leg brace generally used to prevent a thrust of the knee of the wearer P, and includes a placement part 47 and a support part 48. The placement part 47 is inserted into the shoe S worn by the wearer P, and the foot of the wearer P is placed on the placement part 47. The placement part 47 basically has a plate body substantially perpendicular to the up/down direction of the wearer P, and has a connection piece 47a protruding upward from the outer part of the placement part 47.

The support part 48 is disposed on the outside of the lower leg of the wearer P. The support part 48 mainly includes a link extending in the up/down direction of the wearer P, and a lower end part of the support part 48 is rotatably connected to the connection piece 47a of the placement part 47 around an axis extending in the left/right direction of the wearer P.

The above-described support part 48 may be able to adjust the length thereof in the up/down direction of the wearer P, or the tilt angle around the axis extending in the front/rear direction of the wearer P with respect to the placement part 47. However, the structure of the support part 48 is not central part of the present disclosure, the description thereof is thus omitted.

The first pushing part 43 is a pad extending in the up/down direction of the wearer P, and can come into substantial surface contact with a lower area (e.g., a lower side of the ankle bone B1) of the inside of the leg of the wearer P including the ankle. The second pushing part 44 is a pad extending in the up/down direction of the wearer P, and can come into substantial surface contact with the outside of the leg of the wearer P.

The above-described second pushing part 44 is fixed to a part of the support part 48 of the lower leg assisting part 42 on the side opposite to the lower leg of the wearer P. Therefore, the support part 48 of the lower leg assisting part 42 functions as a connection part that connects the placement part 47 of the lower leg assisting part 42 to the second pushing part 44.

The first restraint part 45 is a belt wound around the first and the second pushing parts 43 and 44, the leg of the wearer P, and the support part 48 of the lower leg assisting part 42 so that the first and the second pushing parts 43 and 44 are pushed against the leg. The first restraint part 45 is fixed to the support part 48 of the lower leg assisting part 42 in a state in which it is wound near the lower side of the ankle of the leg of the wearer P by using, for example, a hook-and-loop fastener.

The second restraint part 46 is a belt wound around the first and the second pushing parts 43 and 44, the leg of the wearer P, and a position (i.e., a part) of the support part 48 of the lower leg assisting part 42 above the first restraint part 45 so that the first and the second pushing parts 43 and 44 are pushed against the leg. The second restraint part 46 is fixed to the support part 48 of the lower leg assisting part 42 in a state in which it is wound around the leg of the wearer P under the knee by using, for example, a hook-and-loop fastener.

Regarding the leg brace 41 described above, the wearer P puts on the shoe S, places his/her foot on the placement part 47 of the lower leg assisting part 42, places the first pushing part 43 on the inner side of his/her lower leg so that his/her lower leg is held between the first and the second pushing parts 43 and 44, and winds the first and the second restraint parts 45 and 46 around the first and the second pushing parts 43 and 44, his/her lower leg, and the support part 48 of the lower leg assisting part 42 to thereby fix them, so that the wearer P can wear the leg brace 41.

At this time, the first restraint part 45 causes the first pushing parts 43 to push the vicinity of the lower side of the ankle of the wearer P outward. By doing so, the lower side of the ankle bone B1 is pushed outward, an inclination of the lower leg which inclines inwardly toward the lower side thereof is eliminated and the foot is supinated, and thus the talonavicular joint axis AX1 and the calcaneocuboid joint axis AX2 are corrected so as to be disposed substantially in parallel when viewed from the rear side of the wearer P.

As a result, a kinematic chain of the leg of the wearer P is likely to occur, and when the wearer P tries to pronate his/her foot, the knee is internally rotated through the lower leg by the kinematic chain, so that the moment arm can be reduced. Thus, a knee *varus* moment becomes smaller than that when the wearer P does not wear the leg brace 41, whereby it is possible to reduce a pain in the knee of the wearer P.

Fifth Embodiment

Figure 11:
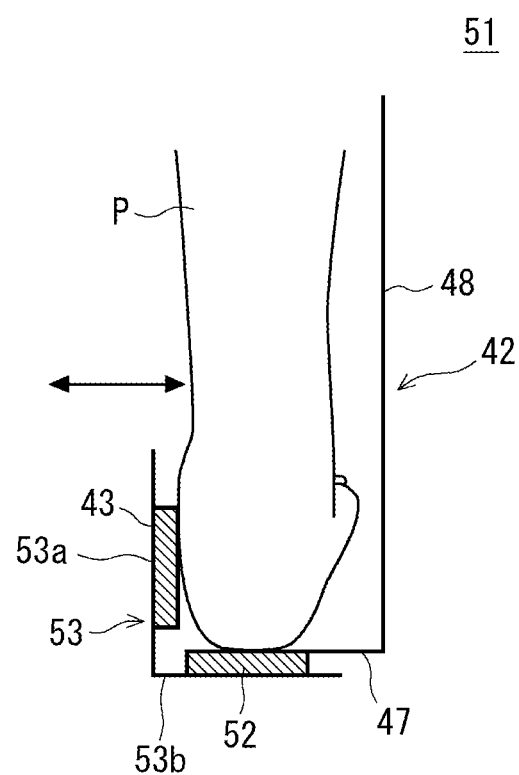
FIG. 11 is a diagram for explaining an operation of the first pushing part of a leg brace according to a fifth embodiment.

FIG. 11 is a diagram for explaining an operation of the first pushing part of a leg brace according to this embodiment. Note that in FIG. 11, in order to make the operation of the first pushing part clear, the second pushing part, the first and the second restraint parts, and the like are omitted.

It should be noted that a leg brace 51 according to this embodiment has a structure substantially the same as that of the leg brace 41 according to the fourth embodiment, and thus redundant descriptions are omitted and the same members are described using the same reference symbols. However, the leg brace 51 according to this embodiment is attached to the right leg of the wearer P.

The leg brace 51 includes an adjustment part 52 capable of adjusting a position of the first pushing part 43 in the left/right direction of the wearer P. At this time, the first and the second restraint parts 45 and 46 in the leg brace 41 according to the fourth embodiment may be omitted, and the leg brace 51 may instead include a restraint part 53 connected to the placement part 47 of the lower leg assisting part 42 via the adjustment part 52.

The restraint part 53 basically has, for example, a substantially L-shaped plate body when viewed from the rear side of the wearer P, and includes a first part 53a extending in the substantially up/down direction of the wearer P and a second part 53b extending in the substantially left/right direction of the wearer P. The first pushing part 43 is provided on the upper part of the surface of the first part 53a facing the wearer P. At this time, the first pushing part 43 is disposed at a position where it can come into substantial surface contact with the lower side of the ankle bone B1 of the wearer P.

The second part 53b is connected to the placement part 47 of the lower leg assisting part 42 via the adjustment part 52. The adjustment part 52 can move the restraint part 53 along a slide groove extending in the left/right direction of the wearer P, and can fix it to a desired position by a ratchet mechanism or the like.

By the above structure, the first pushing part 43 can push the vicinity of the lower side of the ankle of the wearer P outward via the adjustment part 52 and the restraint part 53. As a result, the lower side of the ankle bone B1 is pushed outward, an inclination of the lower leg which inclines inwardly toward the lower side thereof is eliminated and the foot is supinated, and thus the talonavicular joint axis AX1 and the calcaneocuboid joint axis AX2 can be corrected so as to be disposed substantially in parallel when viewed from the rear side of the wearer P.

Further, the degree of pushing of the first pushing part 43 can be adjusted in accordance with the thickness of the lower leg of each individual wearer P, and thus the leg brace 51 has a high versatility.

Note that in the leg brace 51 according to this embodiment, although the alignment of the ankle bone B1 and the heel bone B2 of the wearer P are corrected by the first pushing part 43, the alignment of the ankle bone B1 and the heel bone B2 of the wearer P may be corrected by the second pushing part. In this case, the vicinity of the upper side of the ankle of the wearer P including the ankle thereof (i.e., the upper side of the ankle bone B1) is pushed inward by the second pushing part. Thus, for example, if the structure of the leg brace 51 is left-right reversed, the second pushing part can be positioned on the inside of the leg. However, any structure may be adopted in which the upper side of the ankle bone B1 of the wearer P can be pushed inward by the second pushing part.

Sixth Embodiment

Figure 12:
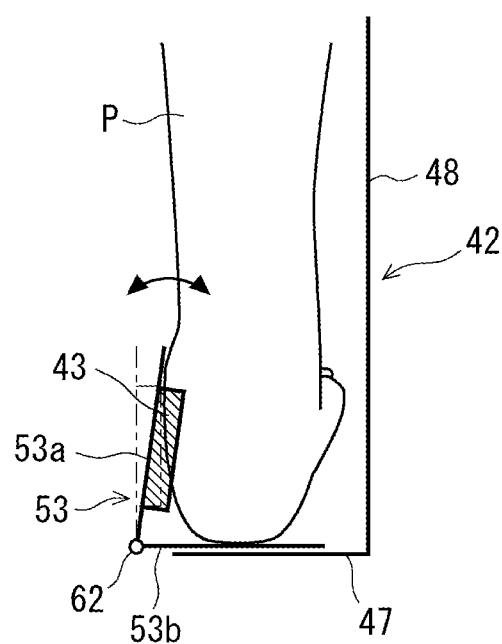
FIG. 12 is a diagram for explaining an operation of the first pushing part of a leg brace according to a sixth embodiment.

FIG. 12 is a diagram for explaining an operation of the first pushing part of a leg brace according to this embodiment. Note that in FIG. 12, in order to make the operation of the first pushing part clear, the second pushing part, the first and the second restraint parts, and the like are omitted. It should be noted that a leg brace 61 according to this embodiment has a structure substantially the same as that of the leg brace 51 according to the fifth embodiment, and thus redundant descriptions are omitted and the same members are described using the same reference symbols.

The leg brace 61 according to this embodiment includes an adjustment part 62 capable of adjusting a tilt angle of the first pushing part 43 with respect to the placement part 47 of the lower leg assisting part 42. In this case, the adjustment part 62 may be provided at a corner between the first and the second parts 53a and 53b of the restraint part 53. Note that the leg brace 61 may include the adjustment part 52 according to the fifth embodiment, or the adjustment part 52 may be omitted and the second part 53b of the restraint part 53 may be fixed to the placement part 47 of the lower leg assisting part 42.

For example, the adjustment part 62 can tilt the first part 53a with respect to the second part 53b around a rotation axis extending in the front/rear direction of the wearer P, and can fix the first part 53a to a desired tilt angle by a ratchet mechanism or the like.

By the above structure, the first pushing part 43 can push the vicinity of the lower side of the ankle of the wearer P outward via the adjustment part 62 and the restraint part 53. As a result, the lower side of the ankle bone B1 is pushed outward, an inclination of the lower leg which inclines inwardly toward the lower side thereof is eliminated and the foot is supinated, and thus the talonavicular joint axis AX1 and the calcaneocuboid joint axis AX2 can be corrected so as to be disposed substantially in parallel when viewed from the rear side of the wearer P.

Further, the degree of pushing of the first pushing part 43 can be adjusted in accordance with the degree of tilt of the lower leg of each individual wearer P, and thus the leg brace 61 has a high versatility.

Note that in the leg brace 61 according to this embodiment, although the alignment of the ankle bone B1 and the heel bone B2 of the wearer P are corrected by the first pushing part 43, the alignment of the ankle bone B1 and the heel bone B2 of the wearer P may be corrected by the second pushing part. In this case, the vicinity of the upper side of the ankle of the wearer P is pushed inward by the second pushing part. Thus, for example, if the structure of the leg brace 61 is left-right reversed, the second pushing part can be tilted so that the vicinity of the upper side of the ankle of the wearer P is pushed inward by the second pushing part. However, any structure may be adopted in which the upper side of the ankle bone B1 of the wearer P can be pushed inward by the second pushing part.

Seventh Embodiment

Figure 13:
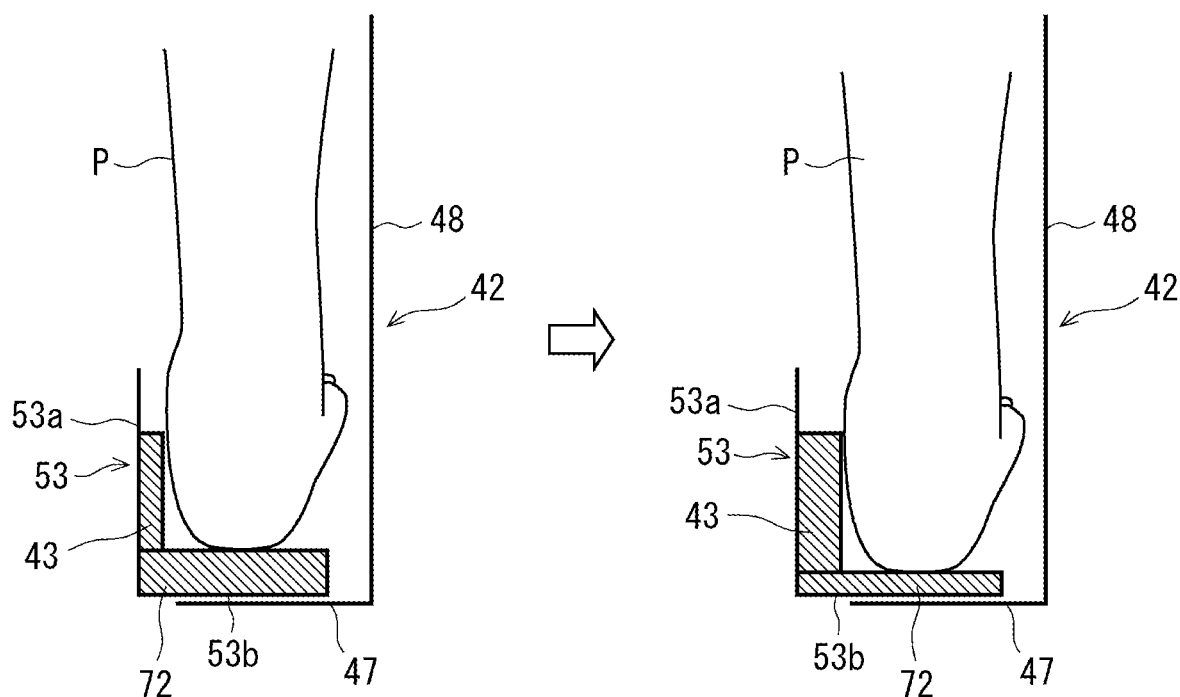
FIG. 13 is a diagram for explaining an operation of the first pushing part of a leg brace according to a seventh embodiment.

FIG. 13 is a diagram for explaining an operation of the first pushing part of a leg brace according to this embodiment, the left side thereof showing the state of the first pushing part before it is deformed, and the right side thereof showing the state of the first pushing part after it is deformed.

Note that in FIG. 13, in order to make the operation of the first pushing part clear, the second pushing part, the first and the second restraint parts, and the like are omitted. It should be noted that a leg brace 71 according to this embodiment has a structure substantially the same as that of the leg brace 51 according to the fifth embodiment, and thus redundant descriptions are omitted and the same members are described using the same reference symbols.

As shown in FIG. 13, the leg brace 71 according to this embodiment includes a filling part 72 that fills an inside of the first pushing part 43 with a filler when the foot of the wearer P is placed on the placement part 47 of the lower leg assisting part 42.

The filling part 72 is provided on the upper surface of the second part 53b of the restraint part 53, and is a bag body filled with water or air. The first pushing part 43 is also a bag body and is connected to the filling part 72 by a forward path and a backward path. In this case, one-way valves may be provided in the forward and the backward paths. Further, each of the first pushing part 43 and the filling part 72 is formed of a material that expands and contracts, such as rubber, and a stronger rubber material may be used for the first pushing part 43 than that used for the filling part 72. When a load is imposed on the filling part 72, the filler in the filling part 72 may be moved to the first pushing part 43, and when the load imposed on the filling part 72 is released, the filler in the first pushing part 43 may be made to return to the filling part 72. By doing the above, not only the impact load of the heel during the walking can be absorbed by the filler, but also the foot part can be corrected so that it is supinated in a stance state during the walking.

In the above-described leg brace 71, as shown in FIG. 13 from the left to the right thereof, when the wearer P places his/her leg on the filling part 72, the first pushing part 43 is filled with the filler in the filling part 72 from the forward path, and the first pushing part 43 comes into contact with the leg of the wearer P.

At this time, the first pushing part 43 pushes the vicinity of the lower side of the ankle of the wearer P outward. By doing so, the lower side of the ankle bone B1 is pushed outward, an inclination of the lower leg which inclines inwardly toward the lower side thereof is eliminated and the foot is supinated, and thus the talonavicular joint axis AX1 and the calcaneocuboid joint axis AX2 can be corrected so as to be disposed substantially in parallel when viewed from the rear side of the wearer P.

Further, the shape of the first pushing part 43 can be made to correspond to the shape of the vicinity of the ankle of each individual wearer P, and thus the leg brace 71 has a high versatility. Note that when the first pushing part 43 is strongly pushed, the filler in the first pushing part 43 can be returned to the filling part 72 from the backward path.

Note that in the leg brace 71 according to this embodiment, although the alignment of the ankle bone B1 and the heel bone B2 of the wearer P are corrected by the first pushing part 43, the alignment of the ankle bone B1 and the heel bone B2 of the wearer P may be corrected by the second pushing part. In this case, the vicinity of the upper side of the ankle of the wearer P including the ankle thereof is pushed inward by the second pushing part. Thus, for example, if the structure of the leg brace 71 is left-right reversed, the second pushing part can be deformed so that the vicinity of the upper side of the ankle of the wearer P is pushed inward by the second pushing part. However, any structure may be adopted in which the upper side of the ankle bone B1 of the wearer P can be pushed inward by the second pushing part.

Note that the present disclosure is not limited to the above-described embodiments and can be modified as appropriate without departing from the spirit of the present disclosure.

For example, in the above-described embodiments, although a patient with medial knee osteoarthritis is exemplified as a person who wears a leg brace, the present disclosure is not limited thereto, and the above-described effects can be enjoyed by attaching the leg brace to a person in whom the talonavicular joint axis AX1 and the calcaneocuboid joint axis AX2 do not cross each other in a stance state.

For example, the leg brace attached to the leg opposite to the leg to which the leg brace is attached in the above-described embodiments may have a structure in which the left and right sides are interchanged with respect to an axis passing through the center of gravity of the leg brace and extending in the front/rear direction as a central axis.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A leg brace that is inserted into a shoe configured to be worn by a wearer and configured to be attached to a leg of the wearer to correct alignment of an ankle bone and a heel bone of the wearer, the leg brace comprising:
    a first pushing part configured to push the leg of the wearer outward so that the ankle bone is positioned above the heel bone;
    a second pushing part configured to push the leg of the wearer inward so that the ankle bone is positioned above the heel bone;
    a restraint part configured to restrain a positional relation between the first and the second pushing parts in which they face each other across the leg of the wearer;
    a placement part for placement of a foot of the wearer, the placement part being connected to the first pushing part or the second pushing part;
    a contact part configured to come into contact with at least a side part of the leg of the wearer above the first and the second pushing parts; and
    a connection part that connects the contact part to the restraint part configured to be disposed on a rear side of a heel of the wearer,
    wherein the first pushing part, the second pushing part, and the restraint part form a substantially U-shape when viewed from an up/down direction, and
    wherein the connection part is able to be deformed in a front/rear direction of the wearer and is not be able to be deformed in a left/right direction of the wearer.

* * * * *